United States Patent
Stevenson et al.

[11] Patent Number: 6,008,980
[45] Date of Patent: Dec. 28, 1999

[54] HERMETICALLY SEALED EMI FEEDTHROUGH FILTER CAPACITOR FOR HUMAN IMPLANT AND OTHER APPLICATIONS

[75] Inventors: Robert A. Stevenson, Canyon Country, Calif.; Donald K. Haskell, Minden; Richard L. Brendel, Carson City, both of Nev.

[73] Assignee: Maxwell Energy Products, Inc., San Diego, Calif.

[21] Appl. No.: 08/969,480

[22] Filed: Nov. 13, 1997

[51] Int. Cl.[6] ........................................ H01G 4/35
[52] U.S. Cl. ...................... 361/302; 361/303; 361/306.1; 361/309
[58] Field of Search ................... 361/302, 306.1, 361/306.2, 303, 307, 320, 321.6, 321.5; 607/2, 5

[56] References Cited

U.S. PATENT DOCUMENTS

| | | |
|---|---|---|
| 2,756,375 | 7/1956 | Peck ........................................ 361/302 |
| 3,235,939 | 2/1966 | Rodriguez et al. .................... 29/25.42 |
| 3,920,888 | 11/1975 | Barr ................................. 174/152 GM |
| 4,083,022 | 4/1978 | Nijman .................................... 333/183 |
| 4,144,509 | 3/1979 | Boutros .................................... 333/178 |
| 4,148,003 | 4/1979 | Colburn et al. .......................... 333/181 |
| 4,152,540 | 5/1979 | Duncan et al. ................ 174/152 GM |
| 4,220,813 | 9/1980 | Kyle ............................... 174/152 GM |
| 4,247,881 | 1/1981 | Coleman .................................. 361/302 |
| 4,314,213 | 2/1982 | Wakino .................................... 333/182 |
| 4,352,951 | 10/1982 | Kyle ................................ 174/152 GM |
| 4,362,792 | 12/1982 | Bowsky et al. .......................... 361/302 |
| 4,421,947 | 12/1983 | Kyle . |
| 4,424,551 | 1/1984 | Stevenson . |
| 4,456,786 | 6/1984 | Kyle . |
| 4,737,601 | 4/1988 | Gartzke . |
| 4,741,710 | 5/1988 | Hogan et al. . |
| 5,032,692 | 7/1991 | DeVolder . |
| 5,070,605 | 12/1991 | Daglow et al. . |
| 5,333,095 | 7/1994 | Stevenson et al. . |
| 5,440,447 | 8/1995 | Shipman et al. ......................... 361/302 |
| 5,539,611 | 7/1996 | Hegner et al. ........................ 361/283.4 |
| 5,670,063 | 9/1997 | Hegner et al. ........................ 219/85.22 |
| 5,825,608 | 10/1998 | Duva et al. .............................. 361/302 |

Primary Examiner—Kristine Kincaid
Assistant Examiner—Eric Thomas
Attorney, Agent, or Firm—Kelly Bauersfeld Lowry & Kelley, LLP

[57] ABSTRACT

An integrated hermetically sealed feedthrough capacitor filter assembly is provided for the shielding and decoupling of a conductive terminal pin or lead of the type used, for example, in an implantable medical device such as a cardiac pacemaker or cardioverter defibrillator against passage of external interference signals, such as caused by digital cellular phones. The simplified feedthrough assembly described herein eliminates the traditional terminal pin subassembly. In this novel approach, the ceramic feedthrough capacitor itself forms a hermetic seal with a conductive pacemaker housing to which it is mounted by welding or brazing. The feedthrough capacitor is configured such that its internal electrodes are not exposed to body fluids, with capacitor electrode plate sets coupled respectively to a conductive ferrule, pin or housing (which may be grounded) and to the non-grounded, or active, terminal pin(s) by conductive adhesive, soldering, brazing, welding or the like. In one preferred form, multiple feedthrough filter capacitors are provided in a substantially coplanar array within a common base structure, with each capacitor in association with a respective terminal pin.

26 Claims, 5 Drawing Sheets

HERMETICALLY SEALED EMI FEEDTHROUGH FILTER CAPACITOR FOR HUMAN IMPLANT AND OTHER APPLICATIONS

BACKGROUND OF THE INVENTION

This invention relates generally to simplified feedthrough capacitor terminal pin subassemblies and related methods of construction, particularly of the type used in implantable medical devices such as cardiac pacemakers and the like, to decouple and shield undesirable electromagnetic interference (EMI) signals from the device. More specifically, this invention relates to a simplified and reduced cost ceramic feedthrough capacitor assembly and related installation method, including one or more filter capacitors which also form the hermetic seal. This eliminates the need for a separate and costly hermetic terminal subassembly which is common in the prior art. In the present invention, the ceramic feedthrough capacitor itself forms the hermetic seal and is adapted particularly for use in connecting a lead wire or electrode through a hermetically sealed housing to internal electronic components of a medical device while decoupling EMI against entry into the sealed housing. This invention is particularly designed for use in cardiac pacemakers (bradycardia devices), cardioverter defibrillators (tachycardia), neurostimulators, internal drug pumps, cochlear implants and other medical implant applications. This invention is also applicable to a wide range of other EMI filter applications, such as military or space electronic modules, where it is desirable to preclude the entry of EMI into a hermetically sealed housing containing sensitive electronic circuitry.

Feedthrough terminal pin assemblies are generally well known in the art for connecting electrical signals through the housing or case of an electronic instrument. For example, in implantable medical devices such as cardiac pacemakers, defibrillators or the like, the terminal pin assembly comprises one or more conductive terminal pins supported by an insulator structure for feedthrough passage from the exterior to the interior of the medical device. Many different insulator structures and related mounting methods are known in the art for use in medical devices wherein the insulator structure provides a hermetic seal to prevent entry of body fluids into the housing of the medical device. However, the feedthrough terminal pins are typically connected to one or more lead wires which effectively act as an antenna and thus tend to collect stray EMI signals for transmission into the interior of the medical device. In the prior art devices, the hermetic terminal pin subassembly has been combined in various ways with a ceramic feedthrough filter capacitor to decouple interference signals to the housing of the medical device. A primary feature of the simplified feedthrough terminal pin subassembly described herein is cost reduction which is accomplished by elimination of the separate hermetic terminal subassembly.

In a typical prior art unipolar construction (as described in U.S. Pat. No. 5,333,095), a round/discoidal (or rectangular) ceramic feedthrough filter capacitor is combined with a hermetic terminal pin assembly to suppress and decouple undesired interference or noise transmission along a terminal pin. The feedthrough capacitor is coaxial having two sets of electrode plates embedded in spaced relation within an insulative dielectric substrate or base, formed typically as a ceramic monolithic structure. One set of the electrode plates is electrically connected at an inner diameter cylindrical surface of the coaxial capacitor structure to the conductive terminal pin utilized to pass the desired electrical signal or signals. The other or second set of electrode plates is coupled at an outer diameter surface of the discoidal capacitor to a cylindrical ferrule of conductive material, wherein the ferrule is electrically connected in turn to the conductive housing of the electronic device. The number and dielectric thickness spacing of the electrode plate sets varies in accordance with the capacitance value and the voltage rating of the coaxial capacitor. The outer feedthrough capacitor electrode plate sets (or "ground" plates) are coupled in parallel together by a metallized layer which is either fired, sputtered or plated onto the ceramic capacitor. This metallized band, in turn, is coupled to the ferrule by conductive adhesive, soldering, brazing, welding, or the like. The inner feedthrough capacitor electrode plate sets (or "active" plates) are coupled in parallel together by a metallized layer which is either glass frit fired or plated onto the ceramic capacitor. This metallized band, in turn, is mechanically and electrically coupled to the lead wire (s) by conductive adhesive or soldering, or the like. In operation, the coaxial capacitor permits passage of relatively low frequency electrical signals along the terminal pin, while shielding and decoupling/attenuating undesired interference signals of typically high frequency to the conductive housing. Feedthrough capacitors of this general type are available in unipolar (one), bipolar (two), tripolar (three), quadpolar (four), pentapolar (five), hexpolar (6) and additional lead configurations. The feedthrough capacitors (in both discoidal and rectangular configurations) of this general type are commonly employed in implantable cardiac pacemakers and defibrillators and the like, wherein the pacemaker housing is constructed from a biocompatible metal such as titanium alloy, which is electrically and mechanically coupled to the hermetic terminal pin assembly which is in turn electrically coupled to the coaxial feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

In the past, feedthrough filter capacitors for cardiac pacemakers and the like, have typically been constructed by preassembly of the coaxial capacitor onto or within a cylindrical or rectangular hermetically sealed terminal pin subassembly which includes the conductive pin and ferrule. More specifically, the terminal pin subassembly is prefabricated to include one or more conductive terminal pins supported within the conductive ferrule by means of a hermetically sealed insulator ring or bead. One type of hermetic terminal pin subassembly which is widely used in implantable medical devices employs an alumina ceramic insulator which, after complicated sputtering/metallization procedures, is gold brazed into a titanium ferrule. In addition, there are platinum lead wires which are also gold brazed to the alumina ceramic insulator to complete the hermetic seal. See for example, the subassemblies disclosed in U.S. Pat. Nos. 3,920,888; 4,152,540; 4,421,947; and 4,424,551. An improved design in the prior art which has substantially improved the volumetric efficiency is based upon surface mounting of a ceramic feedthrough capacitor planar array structure to one outer surface of a hermetic terminal with similar connection to the conductive pins (see the subassemblies disclosed in U.S. Pat. No. 5,333,095). In all of the prior art described above, the feedthrough capacitor is mounted to a separate and relatively costly hermetic terminal pin subassembly.

Although feedthrough filter capacitor assemblies of the type described above have performed in a generally satisfactory manner, the associated manufacturing and assembly costs are unacceptably high. For example, the manufacture of the separate hermetic terminal subassembly is very costly (in most instances the hermetic terminal pin subassembly costs more than the ceramic feedthrough capacitor). In addition, the subsequent installation of the ceramic feedthrough capacitor is time consuming and therefore costly. More particularly, as shown in FIG. 1 of U.S. Pat. No. 4,424,551, installation of the coaxial capacitor into the small annular space between the terminal pin and ferrule can be a difficult and complex multi-step procedure to ensure formation of reliable, high quality electrical connections. The method taught by the 4,424,551 patent teaches the injection of fluidic thermosetting conductive particles into first and second annular cavities (usually by centrifuge operations). This is, however, a time consuming and relatively expensive process.

Accordingly, there is a need for a novel feedthrough filter capacitor assembly that addresses the drawbacks noted above in connection with the prior art. In particular, a novel capacitor assembly is needed which eliminates the fabrication of a separate hermetic terminal pin subassembly and yet may be utilized in many of the same applications, where such subassemblies are now found. Additionally, the improved feedthrough filter capacitor assembly should lend itself to standard manufacturing processes such that cost reductions can be realized immediately. Of course, the new design must be capable of effectively filtering out undesirable electromagnetic interference (EMI) signals from the target device. The present invention fulfills these needs and provides other related advantages.

SUMMARY OF THE INVENTION

The present invention resides in an integrated hermetically sealed feedthrough filter capacitor assembly for shielding and decoupling of a conductive terminal pin or lead of the type used, for example, in an implantable medical device such as a cardiac pacemaker or cardioverter defibrillator against passage of external interference signals, such as caused by digital cellular phones. The feedthrough filter capacitor of the present invention forms a hermetic seal with a conductive substrate to which it is mounted by welding or brazing, thus eliminating the traditional terminal pin subassembly which is common in the prior art. The capacitor assembly is configured such that its internal electrodes are not exposed to body fluids, with capacitor electrode plate sets coupled respectively to the conductive substrate and to the non-grounded or active terminal pin(s) by conductive adhesive, soldering, brazing, welding or the like.

The feedthrough filter capacitor assembly comprises, generally, at least one conductive terminal pin, a conductive substrate through which the terminal pin passes in non-conductive relation, and a feedthrough filter capacitor having first and second electrode plate means and a passageway through which the terminal pin extends in conductive relation with the first electrode plate means. A first hermetic seal joint is provided between the terminal pin and the feedthrough filter capacitor. A second hermetic seal joint is provided between the feedthrough filter capacitor and the conductive substrate, wherein the second electrode plate means is conductively coupled to the conductive substrate.

In a preferred form of the invention, the conductive substrate comprises a stress-relieving flange which generally surrounds the feedthrough filter capacitor and to which the second hermetic seal joint is applied, and a housing to which the flange is attached. In medical implant applications, the housing may be the can that contains an electronic device such as, for example, a cardiac pacemaker. The feedthrough filter capacitor includes a ceramic body which supports the first and second electrode plate means in spaced relation.

The first hermetic seal joint comprises a first metallization layer applied to the feedthrough filter capacitor adjacent to one end of the passageway by sputtering or the like, and a noble metal braze conductively coupling and mechanically attaching the terminal pin to the first metallization layer. The second hermetic seal joint comprises a second metallization layer applied to an exterior surface of the feedthrough filter capacitor by sputtering or the like, and a noble metal braze conductively coupling and mechanically attaching the conductive substrate, and in particular the stress-relieving flange, to the second metallization layer.

The second metallization layer may conductively couple the second electrode plate means with the conductive substrate. Additionally, the second metallization layer may form at least a portion of the second electrode plate means. In an alternative design, the feedthrough filter capacitor may comprises a tubular capacitor which may, if desired, be a multi-layer tubular capacitor. Further, a wire bond pad may be provided which is conductively coupled to the terminal pin. The wire bond pad may be formed on an external surface of the feedthrough filter capacitor.

In another preferred form of the invention, the capacitor assembly includes an alumina wafer which is attached to the ceramic body. In this case, the first hermetic seal joint is formed adjacent to the alumina wafer.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figures 1, 2:
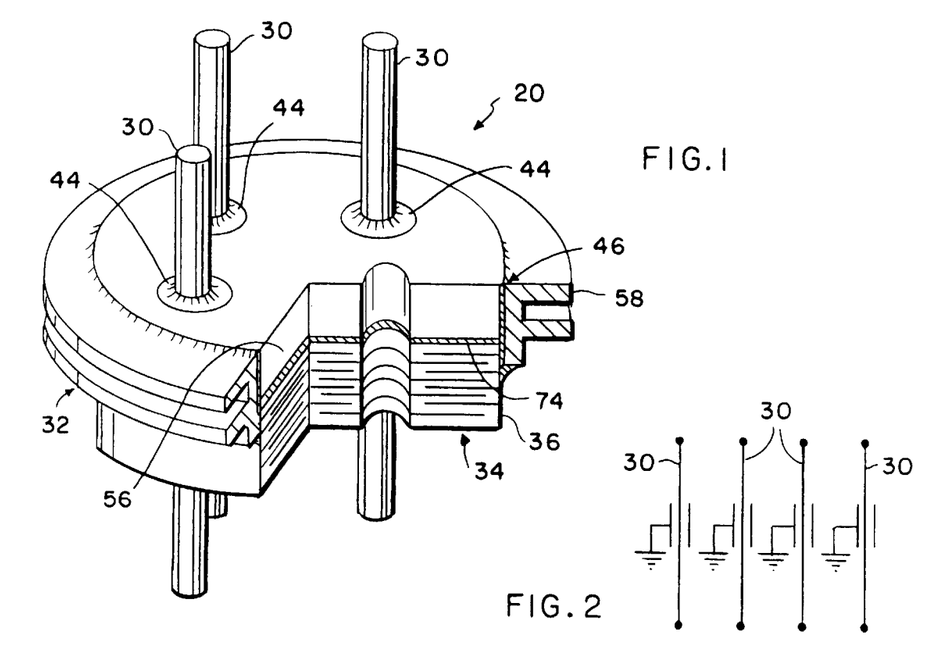
FIG. 1 is a perspective and partially sectional view of a quadpolar feedthrough filter capacitor embodying aspects of the present invention.
FIG. 2 is an electrical schematic of the assembly shown in FIG. 1.
Figure 10:
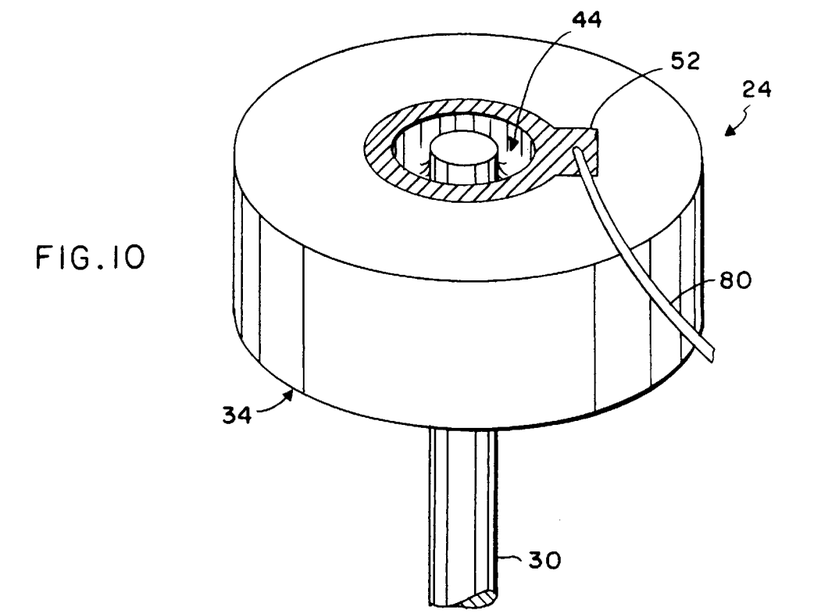
FIG. 10 is a perspective view of an alternate embodiment of a feedthrough filter capacitor assembly embodying aspects of the present invention, wherein the assembly incorporates a unipolar wire bond pad.
Figure 11:
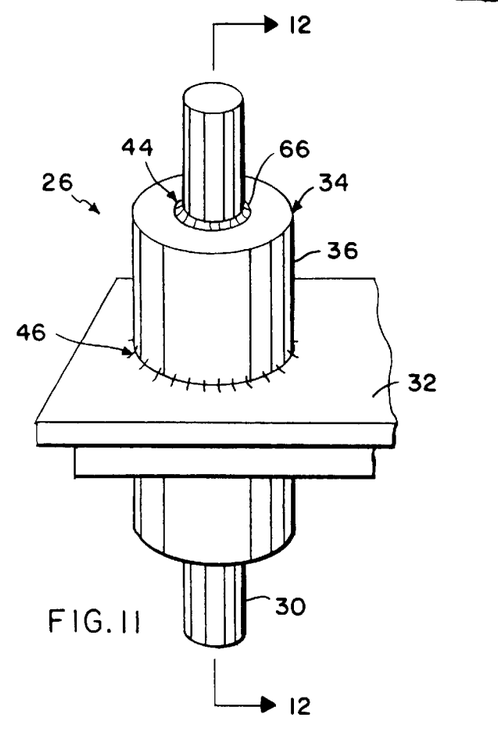
FIG. 11 is a partially fragmented perspective view of a multilayer tubular feedthrough filter capacitor mounted to a conductive substrate in accordance with aspects of the present invention.
Figure 12:
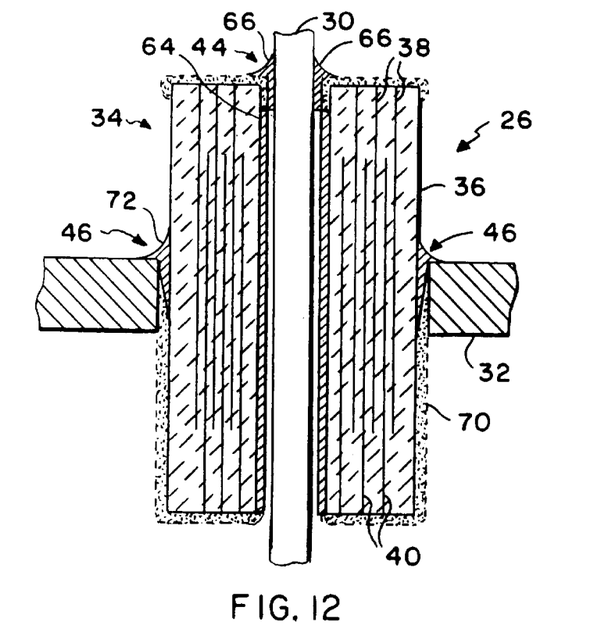
FIG. 12 is an enlarged sectional view taken generally along the line 12—12 of FIG. 11.
Figure 13:
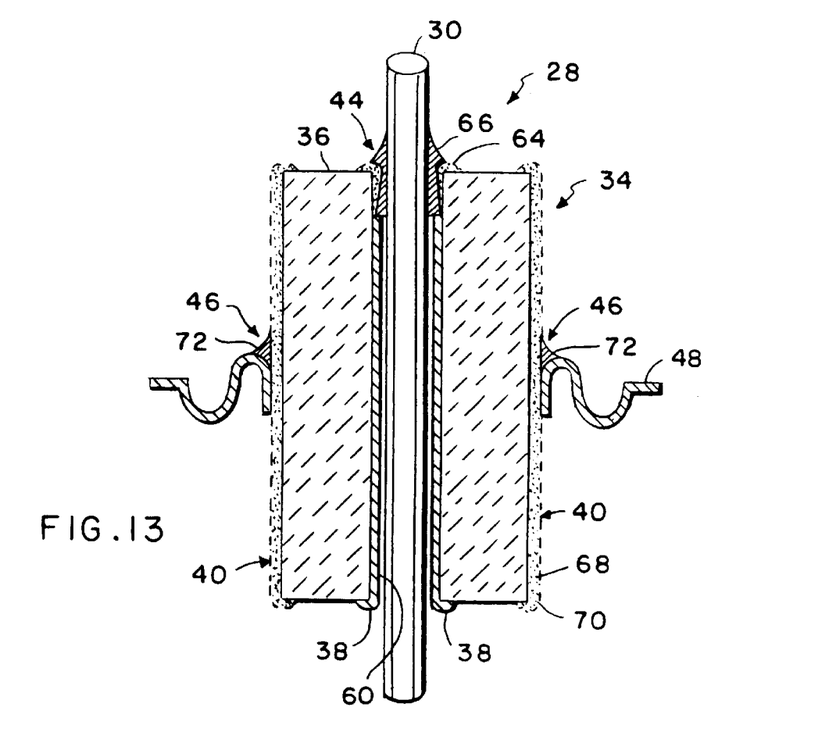
FIG. 13 is a sectional view similar to that illustrated in FIG. 12, illustrating a single layer tubular feedthrough filter capacitor assembly embodying aspects of the present invention, connected to a stress-relieving flange as illustrated in FIG. 9.

As shown in the drawings for purposes of illustration, the present invention is concerned with a novel feedthrough filter capacitor assembly generally designated in FIG. 1 by the reference number 20, in FIGS. 3–8 by the reference number 22, in FIG. 10 by the reference number 24, in FIGS. 11 and 12 by the reference number 26, and in FIG. 13 by the reference number 28. In the following description, functionally equivalent elements of the various embodiments will share the same reference number. The improved feedthrough filter capacitor assemblies 20–28 comprise, generally, at least one conductive terminal pin 30, a conductive substrate 32 through which the terminal pin passes in non-conductive relation, and a ceramic feedthrough filter capacitor 34. The capacitor 34 comprises a ceramic housing 36 that supports in spaced relation first and second electrode plate means 38 and 40. A passageway 42 is provided through the feedthrough filter capacitor 34, through which the terminal pin 30 extends in conductive relation with the first electrode plate means 38. The second electrode plate means 40 is, in turn, conductively coupled to the conductive substrate 32.

In accordance with the present invention, hermetic seal joints 44 and 46 are provided directly between the ceramic feedthrough filter capacitor 34 and, respectively, the conductive terminal pin 30 and the conductive substrate 32, to eliminate the need for a costly separate hermetic terminal pin subassembly. In a preferred embodiment for medical implant applications, the feedthrough filter capacitor assemblies 20–28 provide for shielding and decoupling of the conductive terminal pin 30 or lead of the type used, for example, in a cardiac pacemaker or cardioverter defibrillator, to prevent the passage of externally generated electromagnetic (EM) fields such as interference signals caused by digital cellular phones. The feedthrough filter capacitor 34 may be directly attached, by means of the second hermetic seal joint 46, to a stress-relieving flange 48 that forms a portion of the conductive substrate 32 and which is adapted for mounting onto a conductive pacemaker housing 50 (or other conductive shield structure) by welding, brazing, soldering or adhesive bonding, to support the terminal pin-carrying capacitor 34 assembly for feedthrough passage to the housing interior. Alternative forms of the invention include wire bond pads 52 which facilitate internal lead connections.

The feedthrough filter capacitor assemblies 20–26 are designed such that the sensitive internal electrode plate means 38 and 40 are oriented toward the inside of the implantable device so that they cannot come into contact with body fluids. For human implant applications, a noble metal such as gold is utilized in the hermetic seal joints 44 and 46 to withstand corrosion from body fluids. In addition to medical implant applications, the present invention is also applicable to a wide variety of other EMI filter applications, such as military or space electronic modules, where it is desirable to preclude the entry of EMI into a hermetically sealed housing containing sensitive electronic circuitry.

With reference to FIGS. 1 and 2, there is shown a quadpolar feedthrough filter capacitor assembly constructed in accordance with the principles of the present invention, wherein multiple feedthrough capacitors are provided in a substantially coplanar array within a common base structure, with each capacitor being placed in association with a respective terminal pin. The feedthrough filter capacitor assembly 20 of FIG. 1 provides an example of how the features to be discussed below in connection with the assemblies of FIGS. 3–10 may be easily incorporated into a multi-polar capacitor assembly. Further, the assembly 20 illustrates the use of integrated alumina or capacitor cover layers 54 to provide a buffer between a fluid environment that could be harmful to the internal components of the feedthrough filter capacitor 34. In particular, it is sometimes desirable, especially in medical implant applications, to provide extra ceramic cover layers within the ceramic housing 36 to protect the internal electrode plate means 38 and 40. The capacitor cover layers 54 may be provided as the ceramic housing 36 is manufactured. Alternatively, an alumina wafer 56 may be provided on the outboard side of the ceramic feedthrough filter capacitor housing 36. As will be discussed more fully below in connection with FIG. 6B, the alumina ceramic wafer 56 may be co-fired, glass/frit fired or bonded with non-conductive thermal setting adhesives to the outboard side of the ceramic housing 36. FIG. 1 further illustrates direct attachment between the ceramic feedthrough filter capacitor 34 to a standard H-flange 58. The H-flange 58 would, in turn, be connected to another portion of the conductive substrate 32, such as the pacemaker housing 50 (shown in FIG. 9). The connection between the feedthrough filter capacitor 34 and the H-flange 58 is effected by means of the second hermetic seal joint 46. FIG. 2 illustrates an electrical schematic corresponding to the feedthrough filter capacitor assembly 20 of FIG. 1.

Figures 3, 4:
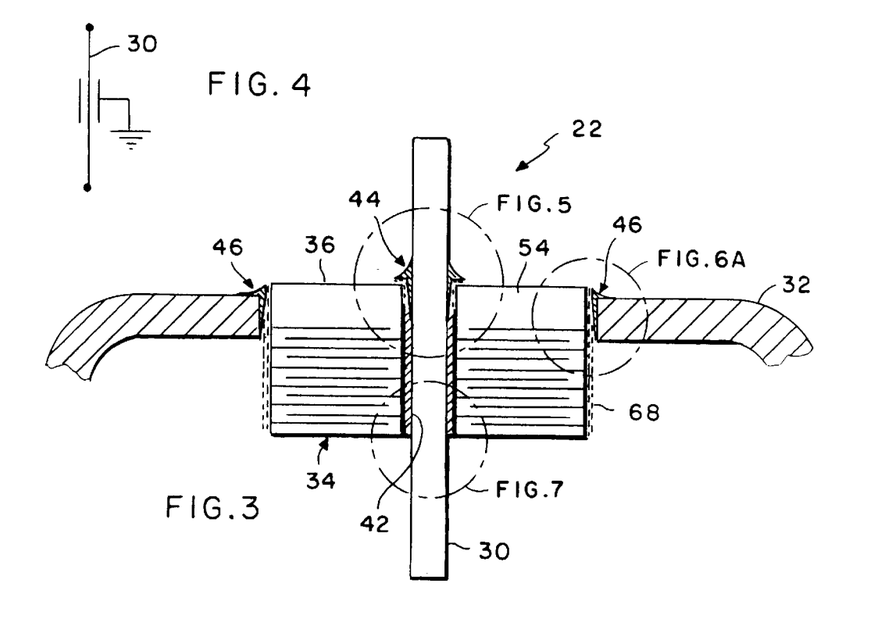
FIG. 3 is a sectional view of a unipolar hermetically sealed feedthrough filter capacitor embodying aspects of the present invention, illustrating a conductive terminal pin extending through a ceramic feedthrough filter capacitor which is, in turn, conductively coupled and mechanically attached to a conductive substrate.
FIG. 4 is an electrical schematic of the assembly shown in FIG. 3.
Figure 5:
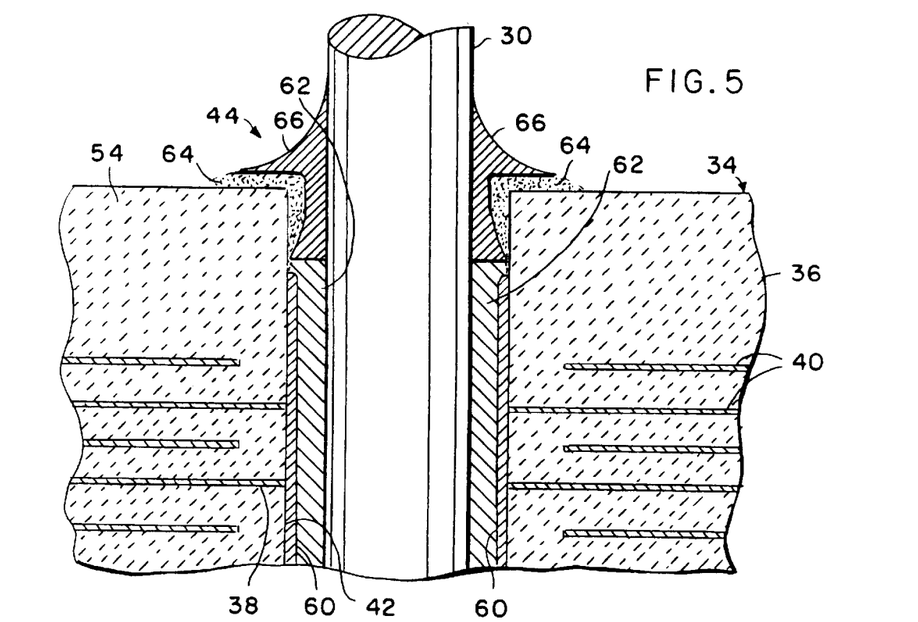
FIG. 5 is an enlarged fragmented sectional view taken generally of the area indicated by the line 5 in FIG. 3, illustrating details of a first hermetic seal joint between the terminal pin and the feedthrough filter capacitor.

With reference to FIGS. 3–5, the specific construction of a unipolar hermetically sealed feedthrough filter capacitor assembly 22 will be described. The conductive terminal pin 30 comprises a platinum-iridium lead or other wire that extends through the passageway 42 of the ceramic housing 36. The first electrode plate means 38 comprises a set of electrode plates extending radially outwardly from the passageway 42. The first set of electrode plates 38 are conductively coupled together by means of, for example, palladium-silver metallization 60 applied to the inner surface of the passageway 42. To insure a uniform conductive connection between the terminal pin 30 and the inner passageway metallization 60, a conductive adhesive filling 62 is provided between the terminal pin and the inner passageway metallization.

With reference to FIG. 5, the first hermetic seal joint 44 between the terminal pin 30 and the ceramic housing 36 of the feedthrough capacitor 34 is illustrated in greater detail. To effect the first hermetic seal joint, a first metallization layer 64 is applied to the ceramic housing 36 adjacent to the upper end of the passageway 42. A metal braze 66 is then applied over the metallization layer 64 to conductively couple and mechanically attach the terminal pin 30 to the metallization layer 64. More particularly, the metallization layer 64 is created by first sputtering down an adhesion layer such as titanium. Next nickel is sputtered or electroplated over the adhesion layer. Finally, and especially in the case of a medical implant application, gold is sputtered or electroplated over the nickel. Alternatively, the metallization layer 64 may be deposited by plasma/electric arc discharge or electro-plating techniques.

Figure 6A:
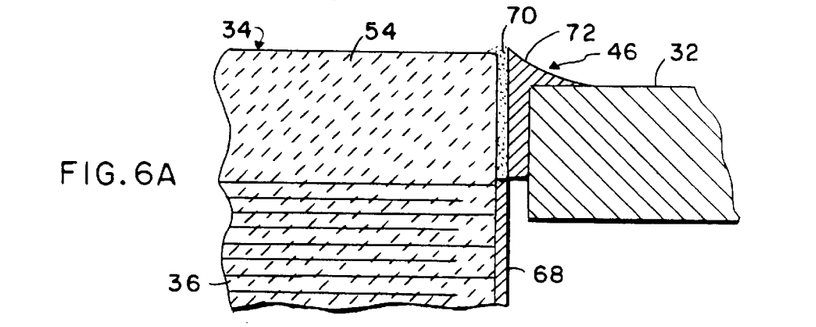
FIG. 6A is an enlarged fragmented elevational view taken of the area indicated by the line 6A in FIG. 3, illustrating a second hermetic seal joint between the feedthrough filter capacitor and the conductive substrate.

Referring to FIG. 6A, it will be seen that the second electrode plate means 40 comprises a set of electrode plates, spaced from the first set of electrode plates 38 and extending from the outer radius of the ceramic housing 36 inwardly. The second set of electrode plates 40 are coupled together by means of an outer metallization layer 68 which may be, for example, similar to the inner passageway metallization 60. Alternatively, the outer metallization layer 68 may be formed in a similar manner to the first metallization layer 64 described above. To effect a conductive and mechanical attachment between the outer periphery of the feedthrough filter capacitor 34 and the conductive substrate 32, a second metallization layer 70 is applied about the periphery of the ceramic housing 36 and adjacent to the outer metallization layer 68 in the same manner as described above in connection with the first metallization layer 64. In particular, an adhesion layer is first sputtered down, such as titanium, after which nickel is sputtered or electroplated over the adhesion layer. Finally, gold is sputtered or electroplated over the nickel layer to complete the second metallization layer in preparation for application of the second metal braze 72. Alternatively, the metallization layer 68 may be deposited by plasma/electric arc discharge or electro-plating techniques. A noble metal braze such as gold is preferred, especially in medical implant applications because of its known characteristics when implanted in the body. It is important that the metal braze conductively couples and mechanically attaches the second metallization layer 70 to the conductive substrate 32. The metal braze 72 may overlap or replace the outer metallization layer 68 to ensure that the second set of electrode plates 40 is conductively coupled, through the metal braze 72, to the conductive substrate 32.

A feature of the present invention is that relatively high dielectric constant materials (for example, barium titanate with a dielectric constant of 2,000) are used to manufacture an integrated ceramic capacitor and hermetic seal. Ceramic dielectric materials such as barium titanate are not as strong as the alumina ceramic typically used to manufacture the hermetic seal subassembly in the prior art. Direct assembly of the ceramic capacitor results in stress to the capacitor due to the mismatch in thermal coefficients of expansion between the titanium pacemaker housing (or other metallic structure 50) and the capacitor dielectric. Particular care must be used to avoid cracking of the capacitor element. Accordingly, the use of dielectric materials with a relatively high modulus of toughness and/or stress relieving designs are desirable.

Figure 6B:
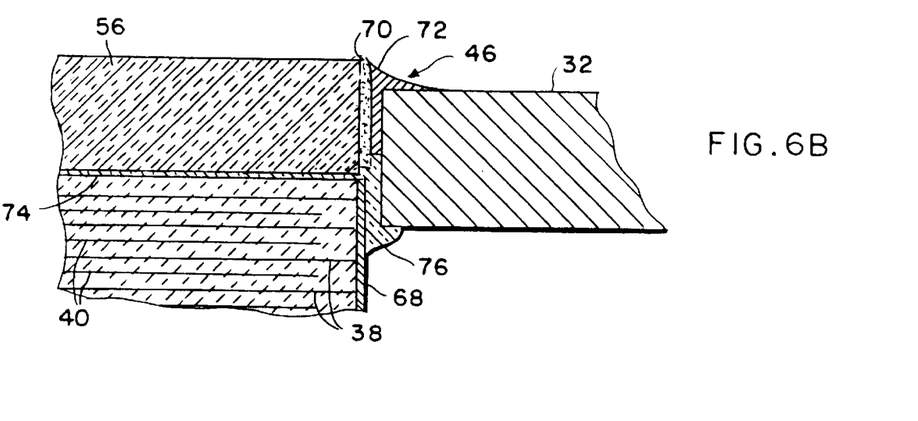
FIG. 6B is an enlarged fragmented elevational section similar to that of FIG. 6A, illustrating an alternative second hermetic seal joint between the feedthrough filter capacitor and the conductive substrate.

FIG. 6B, which is similar to FIG. 6A, illustrates a novel wafer construction which integrates a stronger alumina ceramic layer 56 in the area of the first and second hermetic seal joints 44 and 46, which is able to withstand both welding stresses and the mismatch in thermal coefficients of expansion. The alumina ceramic wafer 56 (also shown in FIG. 1) may be co-fired, glass/frit fired or bonded with non-conductive thermal setting adhesives 74 to the ceramic capacitor housing 36.

As shown in FIG. 6B, the mechanical and conductive attachment between the capacitor 34 and the conductive substrate 32 is similar to that described above. With reference to the second hermetic seal joint 46, an outer metallization layer 68 is provided to conductively couple together with second set of electrode plates 40. The second matallization layer 70 is applied adjacent to the outer metallization layer (or the second metallization layer may replace the outer metallization layer if applied to the entire outer surface of the ceramic housing 36) in the manner described above. The gold braze 72 is then applied to effect the mechanical and conductive coupling between the feedthrough filter capacitor 34 and the conductive substrate 36 which, in this case, is a titanium pacemaker can, header or flange. An additional feature not illustrated in the preceding embodiment is the use of a conductive adhesive 76 between the outer metallization layer 68 and the conductive substrate 32 to help ensure a conductive connection between the second set of electrode plates 40 and the conductive substrate 32.

Figure 7:
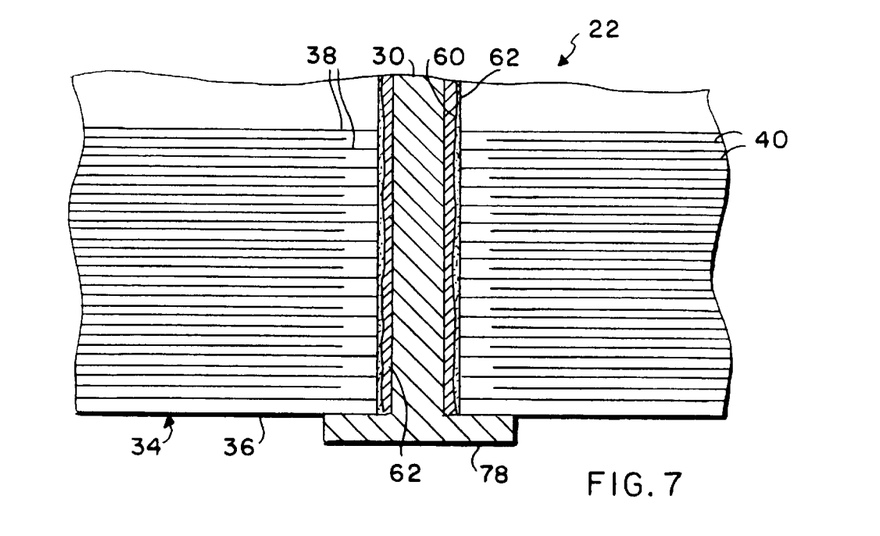
FIG. 7 is an enlarged fragmented elevational section taken of the area indicated by the number 7 in FIG. 3, illustrating use of an optional nail-head-type terminal pin.

FIG. 7 illustrates an alternative configuration of the inboard side of the ceramic feedthrough filter capacitor 34 wherein a nail-head lead 78 provides an optional wire bond pad 80. The pad may be sputtered onto the previously formed lead, plated to the tip of the formed lead wire, or attached by brazing or the like. Further, the wire bond pad may be simply manufactured with the conductive terminal pin 30 in the form of the nail-head lead 78 shown.

Figures 8, 9:
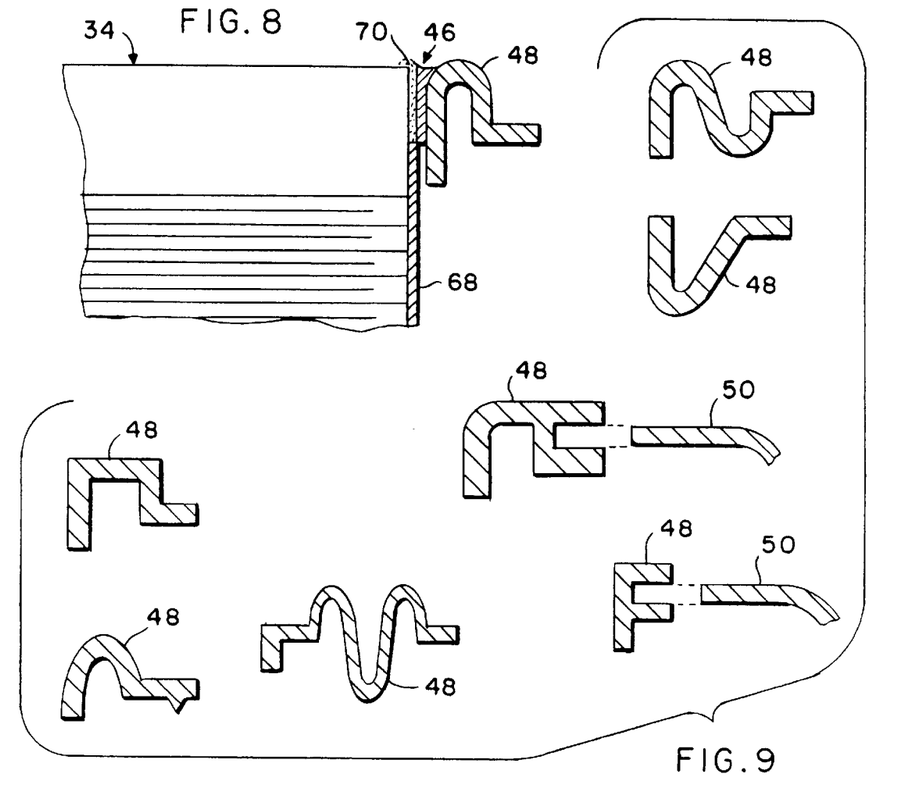
FIG. 8 is a fragmented elevational section similar to FIGS. 6A and 6B, illustrating use of a second hermetic seal joint between the feedthrough filter capacitor and a stress-relieving flange forming a portion of the conductive substrate.
FIG. 9 comprises elevational sectional views of various shaped stress-relieving flanges that may be utilized in the manner illustrated in FIG. 8 to relieve stress at the capacitor outside diameter or perimeter.

FIG. 8 illustrates an alternative embodiment wherein a stress-relieving flange 48 is attached directly to the outer periphery of the ceramic housing 36 by means of the second hermetic seal joint 46. FIG. 9 illustrates a variety of different stress-relieving flange 48 shapes and sizes. An advantage of utilizing stress-relieving flanges is that the integrated feedthrough capacitor/hermetic seal can be manufactured complete with a stress-relieving flange 48 which is ready for installation by welding. The stress-relieving flange 48 may be used in conjunction with either the ceramic feedthrough filter capacitor 34 by itself or with the capacitor/alumina wafer 56 described above.

FIG. 10 shows an alternative to having the lead enter into the inside of the housing. In certain implantable device applications (for example where a flex cable is utilized) it is desirable to wire bond a connection to the capacitor or capacitor substrate. The wire bond pad 80 is formed of gold which is either plated or thick film deposited onto the surface of the ceramic housing 36. The surface of the ceramic housing 36 is prepared for the gold attachment by sputtering, plating or conductive glass frit firing.

FIGS. 11 and 12 show a typical multi-layer tubular capacitor that is attached to both a conductive terminal pin 30 extending centrally therethrough and to a supporting conductive substrate 32 utilizing the first and second hermetic seal joints 44 and 46 of the invention. Tubular capacitors are common in the art and are very inexpensive to fabricate because their geometry lends itself to high volume green ceramic extrusion or rolling processes. Tubular capacitors may be multilayered as illustrated in FIGS. 11 and 12, or single layer (extruded) as illustrated in FIG. 13. The same principles discussed above in connection with attachment of the terminal pin 30 to the ceramic housing 36 by means of a first himitic seal joint 44, and attachment of the ceramic housing to the conductive substrate 32 by means of the second hermitic seal joint 46 described above are equally applicable in the case of a tubular capacitor. Tubular capacitors are very effective high frequency filter elements. Moreover, inductive elements may be added to the inside of the tubular capacitor to form L or Pl type low pass filter surface.

More particularly, with reference to FIG. 12, the first metallization layer 64 is formed over an upper surface of the ceramic housing 36 to conductively couple together the first set of electrode plates 38. The first metallization layer extends partially into the upper end of the passageway 42. Thereafter, the first metal braze 66 is applied to conductively couple together and mechanically attach the upper end of the feedthrough filter capacitor 34 to the terminal pin 30. The second metallization layer is applied over the opposite end of the tubular feedthrough filter capacitor 34 so as to conductively couple together the second set of electrode plates 40. The second metallization layer 70 extends from the lower end of the capacitor 34 on its outer surface upwardly to the point of attachment between the capacitor 34 and the conductive substrate 32. The second metal braze 72 may then be applied over the second metallization layer to conductively couple together and mechanically attach the tubular feedthrough filter capacitor 34 to the conductive substrate 32.

FIG. 13 illustrates a single layer (extruded) tubular capacitor. In this case, the inner passageway metallization 60 functions as the first electrode plate means 38. Adjacent to an upper end of the inner passageway metallization 60 there is applied the first metallization layer 64 by sputtering or the like. The metal braze 66 conductively couples the inner passageway metallization 60 (which is serving as the first electrode plate means 38) to the conductive terminal pin 30. The radially outwardly facing surface of the ceramic housing 36 is sputtered to form the second metallization layer 70 which also serves as the second electrode plate means 40. The stress-relieving flange 48 illustrated may then be conductively coupled and mechanically attached to the second metallization layer 70 by means of the second metal braze 72 as shown.

From the foregoing it will be appreciated that a novel ceramic feedthrough capacitor assembly which also forms a hermetic seal is provided for shielding and decoupling of a conductive terminal pin or lead of the type used, for example, in an implantable medical device such as a cardiac pacemaker or cardioverter defibrillator, to prevent the passage of externally generated electromagnetic (EM) fields such as interference signals caused by additional cellular phones. By integration of the ceramic feedthrough capacitor and hermetic seal into a single unit, the costly separate hermetic terminal subassembly is eliminated. Moreover, the assemblies described above may be utilized in connection with a unipolar feedthrough filter capacitor as well as multiple feedthrough filter capacitors provided in a substantially coplanar array within a common base structure. The use of stress-relieving flanges may further advantageously permit the selection of materials which will withstand both welding stresses and the mismatch in thermal coefficients of expansion inherent in the construction of ceramic feedthrough filter capacitors.

Although several embodiments of the invention have been described in detail for purposes of illustration, various further modifications may be made without departing from the spirit and scope of the invention. For example, the exposed capacitor surface may be overcoated with a non-conductive epoxy or polyamid to enhance its moisture and solvent resistance. Accordingly, the invention is not to be limited, except as by the appended claims.

We claim:

1. A feedthrough filter capacitor assembly, comprising:
   at least one conductive terminal pin;
   a conductive substrate through which the terminal pin passes in non-conductive relation;
   a feedthrough filter capacitor having first and second electrode plate means and a passageway through which the terminal pin extends in conductive relation with the first electrode plate means;
   a first noble metal hermetic seal joint between the terminal pin and the feedthrough filter capacitor; and
   a second noble metal hermetic seal joint between the feedthrough filter capacitor and the conductive substrate, wherein the second electrode plate means is conductively coupled to the conductive substrate.

2. The assembly of claim 1, wherein the second hermetic seal joint comprises a metallization layer applied to an exterior surface of the feedthrough filter capacitor, and a noble metal braze conductively coupling and mechanically attaching the conductive substrate to the metallization layer.

3. The assembly of claim 2, wherein the metallization layer conductively couples the second electrode plate means with the conductive substrate.

4. The assembly of claim 2, wherein the metallization layer forms at least a portion of the second electrode plate means.

5. The assembly of claim 2, wherein the conductive substrate comprises a stress-relieving flange generally surrounding the feedthrough filter capacitor and to which the second hermetic seal joint is applied, and a housing to which the flange is attached.

6. The assembly of claim 1, wherein the feedthrough filter capacitor comprises a tubular capacitor.

7. The assembly of claim 6, wherein the feedthrough filter capacitor comprises a multi-layer tubular capacitor.

8. The assembly of claim 1, wherein the first hermetic seal joint comprises a metallization layer applied to the feedthrough filter capacitor adjacent to one end of the passageway, and a noble metal braze conductively coupling and mechanically attaching the terminal pin to the metallization layer.

9. The assembly of claim 8, including a wire bond pad conductively coupled to the terminal pin.

10. The assembly of claim 9, wherein the wire bond pad is formed on an external surface of the feedthrough filter capacitor.

11. The assembly of claim 8, wherein the feedthrough filter capacitor includes a ceramic body, and wherein the capacitor assembly includes an alumina wafer attached to the ceramic body.

12. The assembly of claim 11, wherein the first hermetic seal joint is formed adjacent to the alumina wafer.

13. A feedthrough filter capacitor assembly, comprising:
    at least one conductive terminal pin;
    a conductive substrate through which the terminal pin passes in non-conductive relation;
    a ceramic feedthrough filter capacitor having first and second electrode plate means and a passageway through which the terminal pin extends in conductive relation with the first electrode plate means;
    a first hermetic seal joint between the terminal pin and the feedthrough filter capacitor, comprising a first metallization layer applied to the feedthrough filter capacitor adjacent to one end of the passageway, and a metal braze conductively coupling and mechanically attaching the terminal pin to the first metallization layer; and a second hermetic seal joint between the feedthrough filter capacitor and the conductive substrate, wherein the second electrode plate means is conductively coupled to the conductive substrate and wherein the second hermetic seal joint comprises a second metallization layer applied to an exterior surface of the feedthrough filter capacitor, and a metal braze conductively coupling and mechanically attaching the conductive substrate to the second metallization layer.

14. The assembly of claim 13, wherein the second metallization layer conductively couples the second electrode plate means with the conductive substrate.

15. The assembly of claim 13, wherein the second metallization layer forms at least a portion of the second electrode plate means.

16. The assembly of claim 13, wherein the conductive substrate comprises a stress-relieving flange generally surrounding the feedthrough filter capacitor and to which the second hermetic seal joint is applied, and a housing to which the flange is attached.

17. The assembly of claim 13, wherein the feedthrough filter capacitor comprises a tubular capacitor.

18. The assembly of claim 17, wherein the feedthrough filter capacitor comprises a multi-layer tubular capacitor.

19. The assembly of claim 13, including a wire bond pad conductively coupled to the terminal pin, wherein the wire bond pad is formed on an external surface of the feedthrough filter capacitor.

20. The assembly of claim 13, wherein the feedthrough filter capacitor includes a ceramic body, the capacitor assembly includes an alumina wafer attached to the ceramic body, and wherein the first hermetic seal joint is formed adjacent to the alumina wafer.

21. The assembly of claim 13, wherein the metal braze comprises a noble metal.

22. A feedthrough filter capacitor assembly, comprising:

at least one conductive terminal pin;

a conductive substrate through which the terminal pin passes in non-conductive relation, the conductive substrate including a stress-relieving flange and a housing to which the flange is attached;

a ceramic feedthrough filter capacitor having a body and first and second electrode plate means embedded within the body, and a passageway through which the terminal pin extends in conductive relation with the first electrode plate means;

a first noble metal hermetic seal joint between the terminal pin and the feedthrough filter capacitor, comprising a first sputtered metallization layer applied to the feedthrough filter capacitor adjacent to one end of the passageway, and a noble metal braze conductively coupling and mechanically attaching the terminal pin to the first sputtered metallization layer; and a second noble metal hermetic seal joint between the feedthrough filter capacitor and the stress-relieving flange, wherein the second electrode plate means is conductively coupled to the stress-relieving flange and wherein the second hermetic seal joint comprises a second sputtered metallization layer applied to an exterior surface of the feedthrough filter capacitor and a noble metal braze conductively coupling and mechanically attaching the stress-relieving flange to the second sputtered metallization layer such that the second sputtered metallization layer conductively couples the second electrode plate means with the conductive substrate.

23. The assembly of claim 22, wherein the second sputtered metallization layer forms at least a portion of the second electrode plate means.

24. The assembly of claim 23, wherein the feedthrough filter capacitor comprises a tubular capacitor.

25. The assembly of claim 23, including a wire bond pad conductively coupled to the terminal pin, wherein the wire bond pad is formed on an external surface of the feedthrough filter capacitor.

26. The assembly of claim 23, including an alumina wafer attached to the body, wherein the first hermetic seal joint is formed adjacent to the alumina wafer.

* * * * *